United States Patent
Takahashi et al.

(10) Patent No.: US 12,215,065 B2
(45) Date of Patent: Feb. 4, 2025

(54) METHODS FOR PRODUCING ARYLAMINE COMPOUND AND ELECTROPHOTOGRAPHIC PHOTOSENSITIVE MEMBER

(71) Applicant: CANON KABUSHIKI KAISHA, Tokyo (JP)

(72) Inventors: Naohiro Takahashi, Chiba (JP); Koichi Nakata, Tokyo (JP); Takuya Kosukegawa, Chiba (JP)

(73) Assignee: Canon Kabushiki Kaisha, Tokyo (JP)

( * ) Notice: Subject to any disclaimer, the term of this patent is extended or adjusted under 35 U.S.C. 154(b) by 129 days.

(21) Appl. No.: 18/047,305

(22) Filed: Oct. 18, 2022

(65) Prior Publication Data

US 2023/0136697 A1  May 4, 2023

(30) Foreign Application Priority Data

Oct. 29, 2021  (JP) .................................. 2021-177592

(51) Int. Cl.
*C07C 209/78* (2006.01)
*G03F 7/031* (2006.01)

(52) U.S. Cl.
CPC ............ *C07C 209/78* (2013.01); *G03F 7/031* (2013.01)

(58) Field of Classification Search
None
See application file for complete search history.

(56) References Cited

U.S. PATENT DOCUMENTS

| | | | |
|---|---|---|---|
| 6,180,303 B1 | 1/2001 | Uematsu et al. | |
| 10,310,395 B2 | 6/2019 | Nakata et al. | |
| 10,558,132 B2 | 2/2020 | Ishiduka et al. | |
| 10,558,133 B2 | 2/2020 | Nakamura et al. | |
| 10,670,979 B2 | 6/2020 | Nakata et al. | |
| 10,761,442 B2 | 9/2020 | Nakata et al. | |
| 10,831,118 B2 | 11/2020 | Watanabe et al. | |
| 11,029,616 B2 | 6/2021 | Kujirai et al. | |
| 11,204,560 B2 | 12/2021 | Tokimitsu et al. | |
| 11,237,494 B2 | 2/2022 | Mori et al. | |
| 2011/0269994 A1* | 11/2011 | Yagi | C07C 227/02 564/434 |
| 2020/0249590 A1 | 8/2020 | Nakata et al. | |

FOREIGN PATENT DOCUMENTS

| | | |
|---|---|---|
| JP | 2000-66425 A | 3/2000 |
| JP | 2010-248099 A | 11/2010 |
| JP | 2018-194794 A | 12/2018 |

OTHER PUBLICATIONS

Jonathan T. Reeves et al., "Synthesis of Trifluoromethyl Ketones from Carboxylic Acids: 4-(3,4-Dibromophenyl)-1,1,1-trifluoro-4-methylpentan-2-one," 89 Org. Synth. 210-219 (Nov. 2011).

Tsutomu Sugasawa et al., "Aminohaloborane in Organic Synthesis. 1. Specific Ortho Substitution Reaction of Anilines," 100(15) J. Am. Chem. Soc. 4842-4852 (1978).).

* cited by examiner

*Primary Examiner* — Sudhakar Katakam
*Assistant Examiner* — Jennifer C Sawyer
(74) *Attorney, Agent, or Firm* — Venable LLP

(57) ABSTRACT

A method for producing an arylamine compound, wherein a chemical compound represented by formula (B) is reacted by addition reaction with a carbon atom having a bound hydrogen atom on a benzene ring of a chemical compound represented by formula (A), in the presence of one or more acids selected from Lewis acids or sulfonic acids; to produce a chemical compound represented by formula (C) including a partial structure represented by formula (D).

15 Claims, No Drawings

METHODS FOR PRODUCING ARYLAMINE COMPOUND AND ELECTROPHOTOGRAPHIC PHOTOSENSITIVE MEMBER

BACKGROUND OF THE INVENTION

Field of the Invention

The present invention relates to a method for producing an arylamine compound and a method for producing an electrophotographic photosensitive member.

Description of the Related Art

As one of charge transport materials that are used in organic devices, an arylamine compound is known which is easily produced and in which the mobility of a hole (positive hole) is high. For the arylamine compound that is used in this organic device, methods of introducing various substituents are adopted for the purpose of exhibiting various functions. (See Japanese Patent Application Laid-Open No. 2018-194794)

In Japanese Patent Application Laid-Open No. 2018-194794, it is proposed to allow an arylamine compound constituting the charge transport material to contain a fluorine atom or a specific fluorinated alkyl group in its structure, for the purpose of reducing affinity for moisture, discharge products and the like and suppressing chemical deterioration.

In Japanese Patent Application Laid-Open No. 2000-66425, it is proposed to introduce a chain-polymerizable group into an arylamine compound constituting a charge transport material, for the purpose of enhancing a film strength of an organic device and improving the abrasion resistance and the scratch resistance. As the chain-polymerizable group, an acryloyloxy group or a methacryloyloxy group is used in many cases, from the viewpoint of ease of handling. As a method for introducing these groups, it is common to produce a reaction product by condensing acrylic acid or an acrylic acid halide with an alcohol form of an arylamine compound which constitutes a charge transport material.

As a method for obtaining the alcohol forms of the arylamine compounds that constitute the above charge transport materials, a synthesis method is proposed which is simple and uses a general-purpose material. (See Japanese Patent Application Laid-Open No. 2010-248099.) In this method, a method is disclosed which produces a precursor of the alcohol form by efficiently introducing a carbon chain into an arylamine skeleton. However, this method passes through a halogenation reaction and Heck reaction, and accordingly, there is a problem that the number of production steps becomes comparatively many. In addition, there has been a problem that the method needs an expensive palladium catalyst as a reaction catalyst, which increases the cost of production.

A method of conjugate adding an α,β-unsaturated carbonyl compound such as acrylic acid or an acrylate ester to an aromatic hydrocarbon in the presence of a Lewis acid such as aluminum chloride is generally referred to as the Friedel-Crafts reaction. (Org. Synth. 2012, 89, 210-219). This reaction is thought not to occur in the case of arylamine. This is because the Lewis acid and the arylamine form a complex, and thereby the electron density of the arylamine decreases. In order to suppress the decrease in the electron density of the arylamine, it is conceivable to use an excessive amount of Lewis acid and activate a reactant such as an α,β-unsaturated carbonyl compound. However, such a successful case has not been known so far.

In addition, there has also been proposed a method of using two Lewis acids (for example, aluminum chloride and boron chloride) and thereby suppressing a decrease in the electron density of the arylamine. (Sugasawa, T. et al. J. Am. Chem. Soc. (See Soc. 1978, 100, 4842)) However, this method is a reaction of acylating an ortho position of an aromatic amine, and a method of conjugate adding an α,β-unsaturated carbonyl compound has not been known so far.

In view of the above points, one aspect of the present disclosure is directed to providing a method for producing an alkyl-esterified arylamine compound by conjugate adding an α,β-unsaturated carbonyl substituent to an arylamine compound that constitutes the charge transport material.

SUMMARY OF THE INVENTION

According to one aspect of the present disclosure, there is provided a method for producing an arylamine compound, wherein a chemical compound represented by the following formula (B) is reacted by addition reaction with a carbon atom having a bound hydrogen atom on a benzene ring of a chemical compound represented by the following formula (A), in the presence of one or more acids selected from Lewis acid or sulfonic acid, to produce a chemical compound represented by the following formula (C) containing a partial structure represented by the following formula (D).

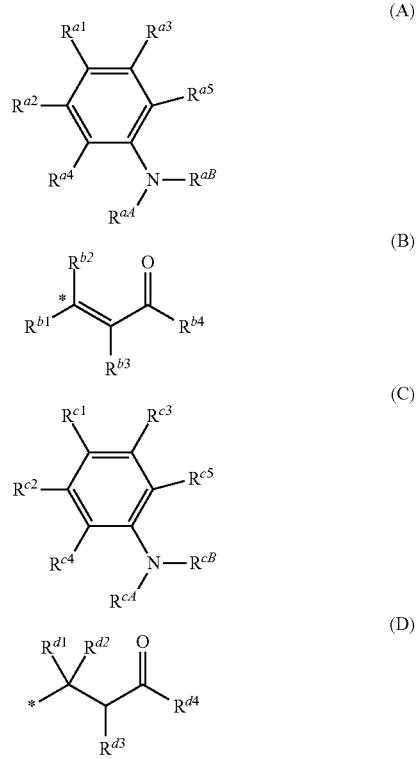

[In the formula (A), $R^{a1}$, $R^{a2}$, $R^{a3}$, $R^{a4}$ and $R^{a5}$ each independently represent a hydrogen atom or an alkyl group. At least one of the $R^{a1}$, $R^{a2}$, $R^{a3}$, $R^{a4}$ and $R^{a5}$ is the hydrogen atom. $R^{aA}$ and $R^{aB}$ each independently represent an unsubstituted or substituted alkyl group, an unsubstituted or substituted aryl group, an acyl group, or an oxycarbonyl group.

In the formula (B), $R^{b1}$, $R^{b2}$ and $R^{b3}$ each independently represent a hydrogen atom or a methyl group. $R^{b4}$ represents a hydrogen atom, a hydroxy group, an unsubstituted or substituted alkoxy group, an unsubstituted or substituted amino group, an unsubstituted or substituted alkyl group, an unsubstituted or substituted aryl group, or an unsubstituted or substituted aryloxy group. The mark * represents a carbon atom position bonding with the formula (A).

In the formula (C), $R^{c1}$, $R^{c2}$, $R^{c3}$, $R^{c4}$ and $R^{c5}$ each independently represent a hydrogen atom, an alkyl group, or a monovalent group represented by the formula (D). $R^{cA}$ and $R^{cB}$ each independently represent an unsubstituted or substituted alkyl group, an unsubstituted or substituted aryl group, an acyl group, or an oxycarbonyl group.

In the formula (D), $R^{d1}$, $R^{d2}$ and $R^{d3}$ each independently represent a hydrogen atom or a methyl group. $R^{d4}$ represents a hydrogen atom, a hydroxy group, an unsubstituted or substituted alkoxy group, an unsubstituted or substituted amino group, an unsubstituted or substituted alkyl group, an unsubstituted or substituted aryl group, or an unsubstituted or substituted aryloxy group. The mark * represents a bonding position.]

According to another aspect of the present disclosure, there is provided a method for producing an electrophotographic photosensitive member, including: producing an arylamine compound represented by the formula (C), formula (F), formula (H), formula (J), formula (L), formula (N), formula (P) or formula (R), by the production method;
reducing a monovalent substituent represented by the formula (D) in the arylamine compound, and converting the substituent into a substituent represented by the following formula(S);
modifying the substituent represented by the following formula(S), and converting the substituent into a substituent represented by the following formula (T) having a cross-linkable group;
obtaining a coating liquid for a surface layer with the obtained arylamine compound;
forming a coating film of the coating liquid for the surface layer; and
curing the coating film to form the surface layer.

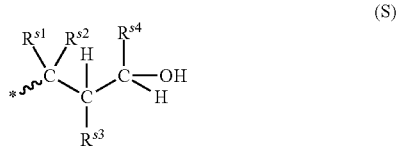

(S)

[In the formula(S), $R^{s1}$, $R^{s2}$ and $R^{s3}$ each independently represent a hydrogen atom or a methyl group. $R^{s4}$ represents a hydrogen atom, an alkyl group or an aryl group. The mark * represents a bonding position.]

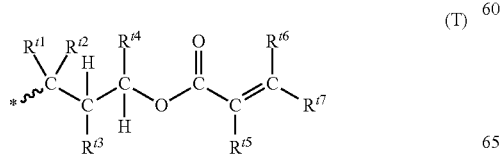

(T)

[In the formula (T), $R^{t1}$, $R^{t2}$ and $R^{t3}$ each independently represent a hydrogen atom or a methyl group. $R^{t4}$ represents a hydrogen atom, an alkyl group or an aryl group. $R^{t5}$, $R^{t6}$ and $R^{t7}$ each independently represent a hydrogen atom or a methyl group. The mark * represents a bonding position.]

According to one aspect of the present disclosure, an alkyl-esterified arylamine compound can be produced by conjugate adding an α,β-unsaturated carbonyl substituent to an arylamine compound that constitutes a charge transport material, in a small number of steps. The production method of the present disclosure has such an advantage that halogenation is not required and the product after the addition reaction is already saturated alkyl chain. Because of this, a method of four stages (halogenation, Heck reaction, reduction of unsaturated bond, and reduction of ester) can be greatly simplified which have been used until now when the alcohol form of the arylamine compound has been synthesized, and the alcohol form of the arylamine compound can be easily produced in as small number of steps as two stages (the present disclosure and reduction of ester). In addition, an electrophotographic photosensitive member can be produced that uses the alkyl-esterified arylamine compound.

Further features of the present invention will become apparent from the following description of exemplary embodiments.

DESCRIPTION OF THE EMBODIMENTS

Preferred embodiments of the present invention will now be described in detail.

Embodiments for carrying out the present invention will be described below, but the scope of the present disclosure is not limited to these embodiments, and modifications in such an extent as not to impair the spirit of the present disclosure are also included in the present invention.

(1)

One embodiment of the present disclosure is a method for producing an arylamine compound, wherein a chemical compound represented by the following formula (B) is reacted by addition reaction with a carbon atom having a bound hydrogen atom on a benzene ring of a chemical compound represented by the following formula (A), in the presence of one or more acids selected from Lewis acids or sulfonic acids, to produce a chemical compound represented by the following formula (C) including a partial structure represented by the following formula (D).

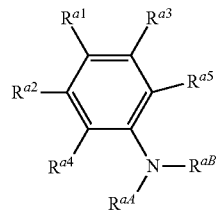

(A)

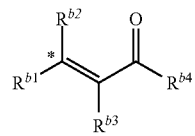

(B)

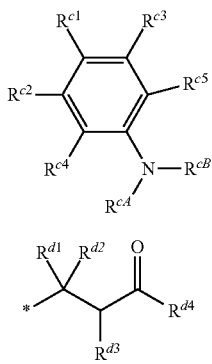

(C)

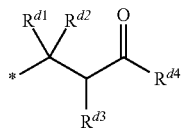

(D)

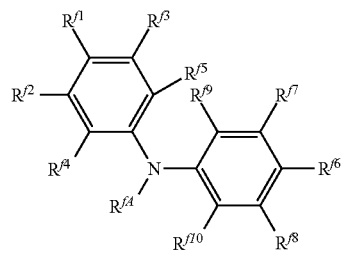

(F)

[In the formula (E), $R^{e1}$, $R^{e2}$, $R^{e3}$, $R^{e4}$, $R^{e5}$, $R^{e6}$, $R^{e7}$, $R^{e8}$, $R^{e9}$ and $R^{e10}$ each independently represent a hydrogen atom or an alkyl group. At least one of the $R^{e1}$, $R^{e2}$, $R^{e3}$, $R^{e4}$, $R^{e5}$, $R^{e6}$, $R^{e7}$, $R^{e8}$, $R^{e9}$ and $R^{e10}$ represents the hydrogen atom. $R^{eA}$ represents an unsubstituted or substituted alkyl group, an unsubstituted or substituted aryl group, an acyl group, or an oxycarbonyl group.

In the formula (F), $R^{f1}$, $R^{f2}$, $R^{f3}$, $R^{f4}$, $R^{f5}$, $R^{f6}$, $R^{f7}$, $R^{f8}$, $R^{f9}$ and $R^{f10}$ each independently represent a hydrogen atom, an alkyl group, or a monovalent group represented by the formula (D). $R^{fA}$ represents an unsubstituted or substituted alkyl group, an unsubstituted or substituted aryl group, an acyl group, or an oxycarbonyl group.]

(3)

[In the formula (A), $R^{a1}$, $R^{a2}$, $R^{a3}$, $R^{a4}$ and $R^{a5}$ each independently represent a hydrogen atom or an alkyl group. At least one of the $R^{a1}$, $R^{a2}$, $R^{a3}$, $R^{a4}$ and $R^{a5}$ is the hydrogen atom. $R^{aA}$ and $R^{aB}$ each independently represent an unsubstituted or substituted alkyl group, an unsubstituted or substituted aryl group, an acyl group, or an oxycarbonyl group.

In the formula (B), $R^{b1}$, $R^{b2}$ and $R^{b3}$ each independently represent a hydrogen atom or a methyl group. $R^{b4}$ represents a hydrogen atom, a hydroxy group, an unsubstituted or substituted alkoxy group, an unsubstituted or substituted amino group, an unsubstituted or substituted alkyl group, an unsubstituted or substituted aryl group, or an unsubstituted or substituted aryloxy group. The mark * represents a carbon atom position bonding with the formula (A).

In the formula (C), $R^{c1}$, $R^{c2}$, $R^{c3}$, $R^{c4}$ and $R^{c5}$ each independently represent a hydrogen atom, an alkyl group, or a monovalent group represented by the formula (D). $R^{cA}$ and $R^{cB}$ each independently represent an unsubstituted or substituted alkyl group, an unsubstituted or substituted aryl group, an acyl group, or an oxycarbonyl group.

In the formula (D), $R^{d1}$, $R^{d2}$ and $R^{d3}$ each independently represent a hydrogen atom or a methyl group. $R^{d4}$ represents a hydrogen atom, a hydroxy group, an unsubstituted or substituted alkoxy group, an unsubstituted or substituted amino group, an unsubstituted or substituted alkyl group, an unsubstituted or substituted aryl group, or an unsubstituted or substituted aryloxy group. The mark * represents a bonding position. The wavy line represents a chemical bond.]

(2)

The chemical compound represented by the formula (A) may be a chemical compound represented by the following formula (E), and the chemical compound represented by the formula (C) may be a chemical compound represented by the following formula (F).

The chemical compound represented by the formula (E) may be a chemical compound represented by the following formula (G), and the chemical compound represented by the formula (F) may be a chemical compound represented by the following formula (H).

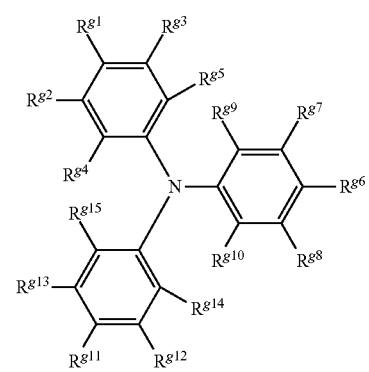

(G)

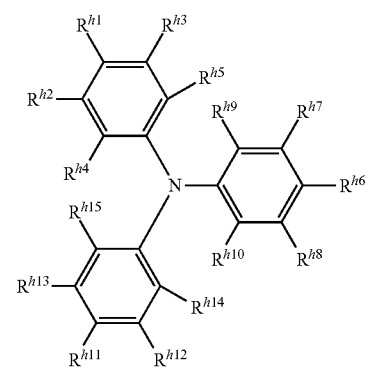

(H)

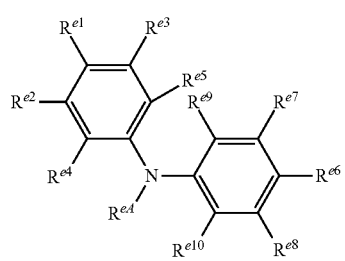

(E)

[In the formula (G), $R^{g1}$, $R^{g2}$, $R^{g3}$, $R^{g4}$, $R^{g5}$, $R^{g6}$, $R^{g7}$, $R^{g8}$, $R^{g9}$, $R^{g10}$, $R^{g11}$, $R^{g12}$, $R^{g13}$, $R^{g14}$ and $R^{g15}$ each independently represent a hydrogen atom or an alkyl group. At least one of the $R^{g1}$, $R^{g2}$, $R^{g3}$, $R^{g4}$, $R^{g5}$, $R^{g6}$, $R^{g7}$, $R^{g8}$, $R^{g9}$, $R^{g10}$, $R^{g11}$, $R^{g12}$, $R^{g13}$, $R^{g14}$ and $R^{g15}$ represents the hydrogen atom.

In the formula (H), $R^{h1}$, $R^{h2}$, $R^{h3}$, $R^{h4}$, $R^{h5}$, $R^{h6}$, $R^{h7}$, $R^{h8}$, $R^{h9}$, $R^{h10}$, $R^{h11}$, $R^{h12}$, $R^{h13}$, $R^{h14}$ and $R^{h15}$ each independently represent a hydrogen atom, an alkyl group, or a monovalent group represented by the formula (D).]

(4)

(4-1)

It is preferable that:

$R^{a1}$ in the formula (A) is a hydrogen atom, and the chemical compound represented by the formula (B) is added selectively to a carbon atom bound to the hydrogen atom to introduce the partial structure represented by the formula (D) and thereby produce the chemical compound represented by the formula (C); or (4-2)

at least one of the $R^{e1}$ and the $R^{e6}$ in the formula (E) is a hydrogen atom, and the chemical compound represented by the formula (B) is added selectively to a carbon atom bound to the hydrogen atom to introduce the partial structure represented by the formula (D) and thereby produce a chemical compound represented by the formula (F); or (4-3)

at least one of the $R^{g1}$, the $R^{g6}$ and the $R^{g11}$ in the formula (G) is a hydrogen atom, and the chemical compound represented by the formula (B) is added selectively to a carbon atom bound to the hydrogen atom to introduce the partial structure represented by the formula (D) and thereby produce a chemical compound represented by the formula (H).

(5)

It is also acceptable to use a chemical compound represented by the following formula (I) in place of the chemical compound represented by the formula (A), and use a chemical compound represented by the following formula (J) in place of the chemical compound represented by the formula (C): and to cause a carbon atom having a bound hydrogen atom on a benzene ring of the chemical compound represented by the following formula (I), to additionally react with the chemical compound represented by the formula (B), in the presence of one or more acids selected from Lewis acids or sulfonic acids, and thereby produce a chemical compound represented by the following formula (J) containing the partial structure represented by the formula (D).

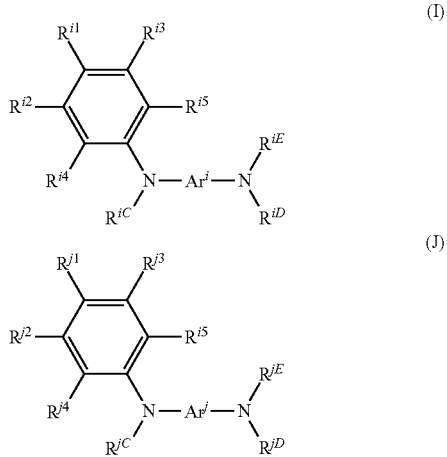

[In the formula (I), $R^{i1}$, $R^{i2}$, $R^{i3}$, $R^{i4}$ and $R^{i5}$ each independently represent a hydrogen atom or an alkyl group. At least one of the $R^{i1}$, $R^{i2}$, $R^{i3}$, $R^{i4}$ and $R^{i5}$ is the hydrogen atom. $R^{iC}$, $R^{iD}$ and $R^{iE}$ each independently represent an unsubstituted or substituted alkyl group, an unsubstituted or substituted aryl group, an acyl group, or an oxycarbonyl group. $Ar^i$ represents an unsubstituted or substituted arylene group, or an unsubstituted or substituted heteroarylene group.

In the formula (J), $R^{j1}$, $R^{j2}$, $R^{j3}$, $R^{j4}$ and $R^{j5}$ each independently represent a hydrogen atom, an alkyl group, or a monovalent group represented by the formula (D). $R^{jC}$, $R^{jD}$ and $R^{jE}$ each independently represent an unsubstituted or substituted alkyl group, an unsubstituted or substituted aryl group, an acyl group, or an oxycarbonyl group. $Ar^j$ represents an unsubstituted or substituted arylene group, or an unsubstituted or substituted heteroarylene group.]

(6)

The chemical compound represented by the formula (I) may be a chemical compound represented by the following formula (K), and the chemical compound represented by the formula (J) may be a chemical compound represented by the following formula (L).

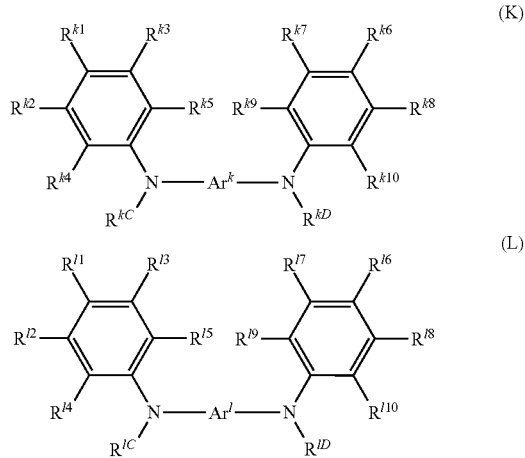

[In the formula (K), $R^{k1}$, $R^{k2}$, $R^{k3}$, $R^{k4}$, $R^{k5}$, $R^{k6}$, $R^{k7}$, $R^{k8}$, $R^{k9}$ and $R^{k10}$ each independently represent a hydrogen atom or an alkyl group. At least one of the $R^{k1}$, $R^{k2}$, $R^{k3}$, $R^{k4}$, $R^{k5}$, $R^{k6}$, $R^{k7}$, $R^{k8}$, $R^{k9}$ and $R^{k10}$ is the hydrogen atom. $R^{kC}$ and $R^{kD}$ each independently represent an unsubstituted or substituted alkyl group, an unsubstituted or substituted aryl group, an acyl group, or an oxycarbonyl group. Ark represents an unsubstituted or substituted arylene group, or an unsubstituted or substituted heteroarylene group.

In formula (L), $R^{l1}$, $R^{l2}$, $R^{l3}$, $R^{l4}$, $R^{l5}$, $R^{l6}$, $R^{l7}$, $R^{l8}$, $R^{l9}$ and $R^{l10}$ each independently represent a hydrogen atom, an alkyl group, or a monovalent group represented by the formula (D). $R^{lC}$ and $R^{lD}$ each independently represent an unsubstituted or substituted alkyl group, an unsubstituted or substituted aryl group, an acyl group, or an oxycarbonyl group. $Ar^l$ represents an unsubstituted or substituted arylene group, or an unsubstituted or substituted heteroarylene group.]

(7)

The chemical compound represented by the formula (I) may be a chemical compound represented by the following formula (M), and the chemical compound represented by the formula (J) may be a chemical compound represented by the following formula (N).

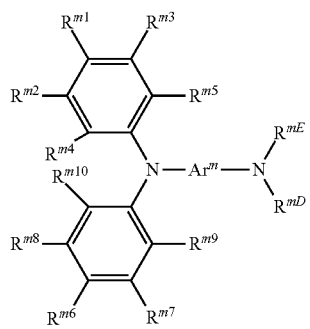

(M)

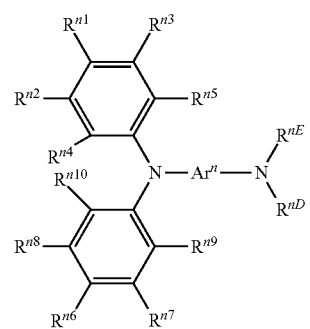

(N)

[In the formula (M), $R^{m1}$, $R^{m2}$, $R^{m3}$, $R^{m4}$, $R^{m5}$, $R^{m6}$, $R^{m7}$, $R^{m8}$, $R^{m9}$ and $R^{m10}$ each independently represent a hydrogen atom or an alkyl group. At least one of the $R^{m1}$, $R^{m2}$, $R^{m3}$, $R^{m4}$, $R^{m5}$, $R^{m6}$, $R^{m7}$, $R^{m8}$, $R^{m9}$ and $R^{m10}$ is the hydrogen atom. $R^{mD}$ and $R^{mE}$ each independently represent an unsubstituted or substituted alkyl group, an unsubstituted or substituted aryl group, an acyl group, or an oxycarbonyl group. $Ar^m$ represents an unsubstituted or substituted arylene group, or an unsubstituted or substituted heteroarylene group.

In the formula (N), $R^{n1}$, $R^{n2}$, $R^{n3}$, $R^{n4}$, $R^{n5}$, $R^{n6}$, $R^{n7}$, $R^{n8}$, $R^{n9}$ and $R^{n10}$ each independently represent a hydrogen atom, an alkyl group, or a monovalent group represented by formula (D). $R^{nD}$ and $R^{nE}$ each independently represent an unsubstituted or substituted alkyl group, an unsubstituted or substituted aryl group, an acyl group, or an oxycarbonyl group. $Ar^n$ represents an unsubstituted or substituted arylene group, or an unsubstituted or substituted heteroarylene group.]

(8)

The chemical compound represented by the formula (K) may be a chemical compound represented by the following formula (O), and the chemical compound represented by the formula (L) may be a chemical compound represented by the following formula (P).

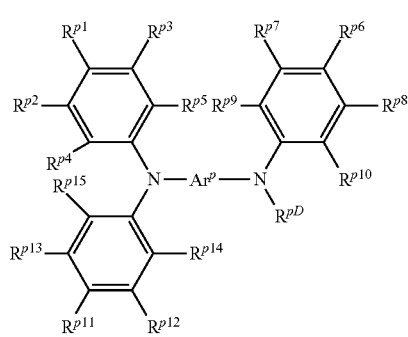

(P)

[In the formula (O), $R^{o1}$, $R^{o2}$, $R^{o3}$, $R^{o4}$, $R^{o5}$, $R^{o6}$, $R^{o7}$, $R^{o8}$, $R^{o9}$, $R^{o10}$, $R^{o11}$, $R^{o12}$, $R^{o13}$, $R^{o14}$ and $R^{o15}$ each independently represent a hydrogen atom or an alkyl group. At least one of the $R^{o1}$, $R^{o2}$, $R^{o3}$, $R^{o4}$, $R^{o5}$, $R^{o6}$, $R^{o7}$, $R^{o8}$, $R^{o9}$, $R^{o10}$, $R^{o11}$, $R^{o12}$, $R^{o13}$, $R^{o14}$ and $R^{o15}$ is the hydrogen atom. $R^{oD}$ represents an unsubstituted or substituted alkyl group, an unsubstituted or substituted aryl group, an acyl group, or an oxycarbonyl group. $Ar^o$ represents an unsubstituted or substituted arylene group, or an unsubstituted or substituted heteroarylene group.

In the formula (P), $R^{p1}$, $R^{p2}$, $R^{p3}$, $R^{p4}$, $R^{p5}$, $R^{p6}$, $R^{p7}$, $R^{p8}$, $R^{p9}$, $R^{p10}$, $R^{p11}$, $R^{p12}$, $R^{p13}$, $R^{p14}$ and $R^{p15}$ each independently represent a hydrogen atom, an alkyl group, or a monovalent group represented by the formula (D). $R^{pD}$ represents an unsubstituted or substituted alkyl group, an unsubstituted or substituted aryl group, an acyl group, or an oxycarbonyl group. $Ar^p$ represents an unsubstituted or substituted arylene group, or an unsubstituted or substituted heteroarylene group.]

(9)

The chemical compound represented by the formula (O) may be a chemical compound represented by the following formula (Q), and the chemical compound represented by the formula (P) may be a chemical compound represented by the following formula (R).

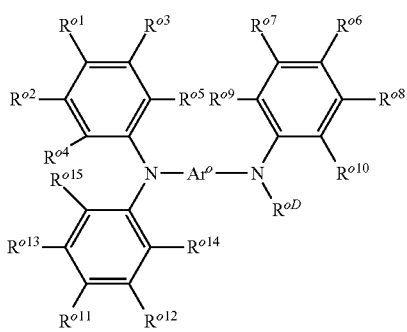

(O)

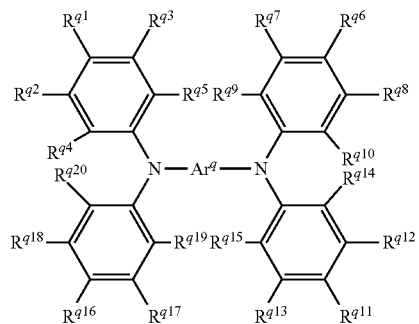

(Q)

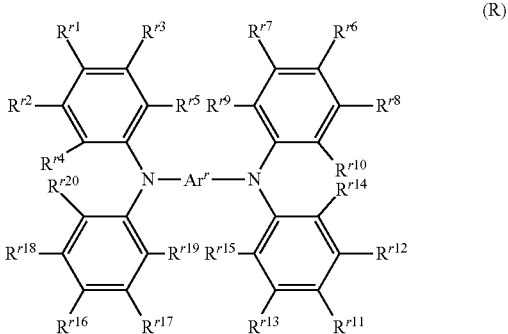

(R)

[In the formula (Q), $R^{q1}$, $R^{q2}$, $R^{q3}$, $R^{q4}$, $R^{q5}$, $R^{q6}$, $R^{q7}$, $R^{q8}$, $R^{q9}$, $R^{q10}$, $R^{q11}$, $R^{q12}$, $R^{q13}$, $R^{q14}$, $R^{q15}$, $R^{q16}$, $R^{q17}$, $R^{q18}$, $R^{q19}$ and $R^{q20}$ each independently represent a hydrogen atom or an alkyl group. At least one of the $R^{q1}$, $R^{q2}$, $R^{q3}$, $R^{q4}$, $R^{q5}$, $R^{q6}$, $R^{q7}$, $R^{q8}$, $R^{q9}$, $R^{q10}$, $R^{q11}$, $R^{q12}$, $R^{q13}$, $R^{q14}$, $R^{q15}$, $R^{q16}$, $R^{q17}$, $R^{q18}$, $R^{q19}$ and $R^{q20}$ is the hydrogen atom. $Ar^q$ represents an unsubstituted or substituted arylene group, or an unsubstituted or substituted heteroarylene group.

In the formula (R), $R^{r1}$, $R^{r2}$, $R^{r3}$, $R^{r4}$, $R^{r5}$, $R^{r6}$, $R^{r7}$, $R^{r8}$, $R^{r9}$, $R^{r10}$, $R^{r11}$, $R^{r12}$, $R^{r13}$, $R^{r14}$, $R^{r15}$, $R^{r16}$, $R^{r17}$, $R^{r18}$, $R^{r19}$ and $R^{r20}$ each independently represent a hydrogen atom, an alkyl group, or a monovalent group represented by the formula (D). $Ar^r$ represents an unsubstituted or substituted arylene group, or an unsubstituted or substituted heteroarylene group.]

(10)

(10-1)

It is preferable that:

$R^{i1}$ in the formula (I) is a hydrogen atom, and the chemical compound represented by the formula (B) is added selectively to a carbon atom bound to the hydrogen atom to introduce a partial structure represented by the formula (D) and thereby produce the chemical compound represented by the formula (J); or (10-2)

at least one of the $R^{k1}$ and the $R^{k6}$ in the formula (K) is a hydrogen atom, and the chemical compound represented by the formula (B) is added selectively to a carbon atom bound to the hydrogen atom to introduce the partial structure represented by the formula (D) and thereby produce a chemical compound represented by the formula (L); or (10-3)

at least one of the $R^{m1}$ and the $R^{m6}$ in the formula (M) is a hydrogen atom, and the chemical compound represented by the formula (B) is added selectively to a carbon atom bound to the hydrogen atom to introduce the partial structure represented by the formula (D) and thereby produce a chemical compound represented by the formula (N); or (10-4)

at least one of the $R^{o1}$, the $R^{o6}$ and the $R^{o11}$ in the formula (O) is a hydrogen atom, and the chemical compound represented by the formula (B) is added selectively to a carbon atom bound to the hydrogen atom to introduce the partial structure represented by the formula (D) and thereby produce a chemical compound represented by the formula (P); or (10-5)

at least one of the $R^{q1}$, the $R^{q6}$, the $R^{q11}$ and the $R^{q16}$ in the formula (Q) is a hydrogen atom, and the chemical compound represented by the formula (B) is added selectively to a carbon atom bound to the hydrogen atom to introduce the partial structure represented by the formula (D) and thereby produce a chemical compound represented by the formula (R).

(11)

It is preferable to add the same equivalent of alcohol as that of the Lewis acid used in the production method of any one of (1) to (10).

(12)

As the alcohol, it is preferable to add a monohydric alcohol having 4 or less carbon atoms, or a dihydric alcohol having 4 or less carbon atoms.

(13)

As the Lewis acid, it is preferable to use one or more Lewis acids selected from the group consisting of aluminum chloride, aluminum bromide, and boron trifluoride.

(14)

As the Lewis acids, it is preferable to use two or more different Lewis acids at the same time.

(15)

As the Lewis acids, it is preferable to use aluminum chloride and boron trifluoride at the same time.

(16)

As the sulfonic acid, it is preferable to use one or more sulfonic acids selected from the group consisting of methanesulfonic acid, trifluoromethanesulfonic acid and camphorsulfonic acid.

(17)

It is preferable to use the Lewis acid and the sulfonic acid at the same time.

(18)

It is preferable to simultaneously use aluminum chloride and boron trifluoride as the Lewis acids, and simultaneously use one or more sulfonic acids selected from the group consisting of methanesulfonic acid and camphorsulfonic acid as the sulfonic acids.

(19)

It is also acceptable to produce a chemical compound represented by the formula (C), the formula (F), the formula (H), the formula (J), the formula (L), the formula (N), the formula (P) or the formula (R), by the production method according to any one of (1) to (18), and reduce a monovalent substituent represented by the formula (D) in each of the chemical compounds to convert the substituent into a substituent represented by the following formula(S).

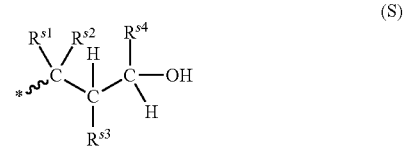

(S)

[In the formula(S), $R^{s1}$, $R^{s2}$ and $R^{s3}$ each independently represent a hydrogen atom or a methyl group. $R^{s4}$ represents a hydrogen atom, an alkyl group or an aryl group. The mark * represents a bonding position. The wavy line represents a chemical bond.]

(20)

It is also acceptable to modify the substituent represented by the formula(S) in the chemical compound obtained by the production method according to (19) to convert the substituent into a substituent represented by the following formula (T) having a cross-linkable group.

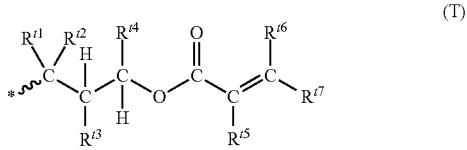

(T)

[In the formula (T), $R^{t1}$, $R^{t2}$ and $R^{t3}$ each independently represent a hydrogen atom or a methyl group. $R^{t4}$ represents a hydrogen atom, an alkyl group or an aryl group. $R^{t5}$, $R^{t6}$ and $R^{t7}$ each independently represent a hydrogen atom or a methyl group. The mark * represents a bonding position. The wavy line represents a chemical bond.]

(21)

An electrophotographic photosensitive member can be produced by a production method including: obtaining an arylamine compound containing a substituent represented by the above formula (T), by the production method according to (20);

obtaining a coating liquid for a surface layer with the obtained arylamine compound;

forming a coating film of the coating liquid for the surface layer; and curing the coating film to form the surface layer.

The present invention will be described in detail below.

First, the Lewis acid will be described which enables the above reaction to proceed in the production method of the present invention. The Lewis acid refers to a substance that receives an electron pair.

In general, there is a case where acids that release proton H+ (sulfuric acid, nitric acid, and the like) are classified as Broensted acids, and substances that do not release the proton H+ but receive electron pairs are classified as Lewis acids. Also in the present application, the present invention is described based on the classification as in the above.

Accordingly, the Lewis acids which will be described in the present application do not include the Broensted acids. The Lewis acid is a substance that receives an electron pair without releasing the proton H+.

The Lewis acid of the present invention has a structure in which a metal atom serving as a center and an electron-attracting group are bonded to each other. Examples of the electron attractive group include a halogen atom such as fluorine, chlorine, bromine or iodine, and a trifluoromethanesulfonate group $CF_3SO_3$ (triflate).

Examples of the Lewis acids include the following. Examples include metal halides and metal triflates such as $AlCl_3$, $AlBr_3$, $AlF_3$, $BF_3 \cdot OEt_2$, $BCl_3$, $BBr_3$, $GaCl_3$, $GaBr_3$, $InCl_3$, $InBr_3$, $In(OTf)_3$, $SnCl_4$, $SnBr_4$, $AgOTf$, $ScCl_3$, $Sc(OTf)_3$, $ZnCl_2$, $ZnBr_2$, $Zn(OTf)_2$, $MgCl_2$, $MgBr_2$, $Mg(OTf)_2$, $LiOTf$, $NaOTf$, $KOTf$, $MesSiOTf$, $Cu(OTf)_2$, $CuCl_2$, $YCl_3$, $Y(OTf)_3$, $TiCl_4$, $TiBr_4$, $ZrCl_4$, $ZrBr_4$, $FeCl_3$, $FeBr_3$, $CoCl_3$ and $CoBr_3$. Among the above Lewis acids, $AlCl_3$, $AlBr_3$, $BF_3 \cdot OEt_2$ and $BCl_3$ are preferable.

In the present invention, various sulfonic acids may be used in addition to the above Lewis acids. The sulfonic acid is an organic acid represented by R—$SO_3H$, and is a Broensted acid. There are various Broensted acids, but Broensted acids which have been recognized to be effective in the reaction of the present invention are sulfonic acid compounds.

It is considered that the sulfonic acid is a strong acid among organic acids, has also an organic group represented by R in the above formulae, accordingly has high compatibility with a reaction substrate which is an organic compound, and accordingly has exhibited the effect of the present invention.

Examples of the sulfonic acids include methanesulfonic acid, ethanesulfonic acid, 1-propanesulfonic acid, trifluoromethanesulfonic acid, benzenesulfonic acid, p-toluenesulfonic acid, dodecylbenzenesulfonic acid, and camphorsulfonic acid. Among the sulfonic acids, methanesulfonic acid, trifluoromethanesulfonic acid and camphorsulfonic acid are preferable.

As for the amount of the Lewis acid or the sulfonic acid to be added, it is desirable to add equivalent amounts to the number of nitrogen atoms and the number of reaction points in the arylamine, or more, considering that the arylamine forms a complex with each of the acids and the reactivity results in being lowered. For example, in the monoamines of (A), (E) and (G), there is one nitrogen atom, and accordingly, it is desirable to add 2 equivalents or more when the reaction point is one, and 3 equivalents or more when the reaction points are two. In addition, in the bisamines of (I), (K), (M), (O) and (Q), there are two nitrogen atoms, and accordingly, it is desirable to add 3 equivalents or more when the reaction point is one, and 4 equivalents or more when the reaction points are two.

In order to enhance the reactivity, different Lewis acids may be combined and used at the same time. The combination of the different Lewis acids is not particularly limited, but $AlCl_3$ and $BF_3 \cdot OEt_2$ are desirable. At this time, the ratio between the amounts of different Lewis acids to be added is not particularly limited, but it is desirable to use the same equivalent amount.

In the present invention, the above reaction can be carried out without a solvent, but it is preferable to use a solvent. The solvent is not particularly limited, but it is preferable to use an aromatic solvent (toluene, xylene, chlorobenzene, orthodichlorobenzene, nitrobenzene, mesitylene, or the like), a hydrocarbon solvent (hexane, cyclohexane, heptane, terpinolene, or the like), and a halogen-based hydrocarbon solvent (dichloromethane, dichloroethane, chloroform, or the like). Furthermore, a plurality of solvents may be used in combination.

In the present invention, alcohol can be added as an additive in order to enhance the reactivity. The alcohol is not particularly limited, but from the viewpoint of the reactivity, a monohydric alcohol having 4 or less carbon atoms or a dihydric alcohol having 4 or less carbon atoms is desirable. (Examples thereof include methanol, ethanol, 1-propanol, 1-butanol, 2-propanol, 2-butanol, t-butanol, and ethylene glycol.)

The amount of the alcohol to be added is not particularly limited, but when a monohydric alcohol is used, it is desirable to use the same equivalent as that of the Lewis acid which has been used in the above reaction, from the viewpoint of the reactivity. In addition, when a dihydric alcohol is used, it is desirable to use half the equivalent of that of the Lewis acid used.

Subsequently, the above formulae (A), (C), (E), (E), (F), (G), (H), (I), (J), (K), (L), (M) (N), (O), (P), (Q) and (R) will be described.

Examples of the alkyl group contained in each of the above chemical compounds include the following groups: a methyl group, an ethyl group, an n-propyl group, an isopropyl group, an n-butyl group, an isobutyl group, a sec-butyl group, a tert-butyl group, an n-pentyl group, an isopentyl group, a neopentyl group, a tert-pentyl group, a cyclopentyl group, an n-hexyl group, a 1-methylpentyl group, a 4-methyl-2-pentyl group, a 3,3-dimethylbutyl group, a 2-ethylbutyl group, a cyclohexyl group, a 1-methylhexyl group, a cyclohexylmethyl group, and a 4-tert-butylcyclohexyl group.

Examples of the aryl group include a phenyl group, a biphenylyl group, a naphthyl group, a fluorenyl group, an anthracenyl group, a phenanthrenyl group, a fluoranthenyl group, a pyrenyl group, and a triphenylenyl group. Furthermore, the aryl group may be a chemical compound having a structure in which these condensed polycyclic structures each having a conjugated structure are connected directly or through a conjugated double bond group.

Examples of the heteroaryl group include a furanyl group, a thiophenyl group, a benzofuranyl group, a dibenzofuranyl group, an imidazolyl group, a pyridyl group, and a quinolyl group.

Examples of the arylene group include a phenylene group, a biphenylylene group, a naphthylene group, a fluorenylene group, an anthracenylene group, a phenanthrenylene group, a fluorantenylene group, a pyrenylene group, and a triphenylenylene group.

Examples of the arylene group include a furanylene group, a thiophenylene group, a benzofuranylene group, a dibenzofuranylene group, an imidazolylene group, a pyridylene group, and a quinolylene group.

Examples of the acyl group include a formyl group, an acetyl group, a propionyl group, and a benzoyl group.

The oxycarbonyl group is a substituent in which a carbonyl group and an alkoxy group are bonded, and represents a carboxylic acid and an ester derived therefrom. Specific examples thereof include the following groups: a methoxycarbonyl group, an ethoxycarbonyl group, a propyloxycarbonyl group, an isopropyloxycarbonyl group, a 1-butyloxycarbonyl group, a 2-butyloxycarbonyl group, a tert-butyloxycarbonyl group, an allyloxycarbonyl group, and a benzyloxycarbonyl group.

Subsequently, the above formula (B) will be described. In the formula (B), $R^{b1}$, $R^{b2}$ and $R^{b3}$ each independently represent a hydrogen atom or a methyl group. $R^{b4}$ represents a hydrogen atom, a hydroxy group, an unsubstituted or substituted alkoxy group, an unsubstituted or substituted amino group, an unsubstituted or substituted alkyl group, an unsubstituted or substituted aryl group, or an unsubstituted or substituted aryloxy group. In particular, the alkoxy group is preferable. Specific examples thereof will be shown below, but the present invention is not limited to the following exemplary compounds. For information, Me represents a methyl group, Et represents an ethyl group, Bu represents a butyl group, and Ph represents a phenyl group.

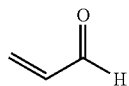

B-1

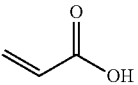

B-2

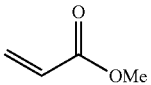

B-3

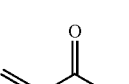

B-4

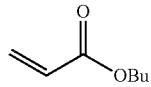

B-5

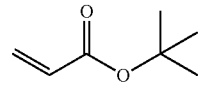

B-6

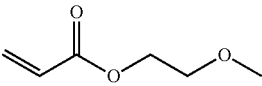

B-7

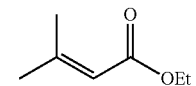

B-8

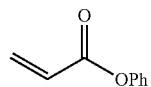

B-9

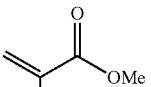

B-10

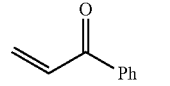

B-11

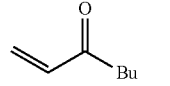

B-12

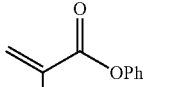

B-13

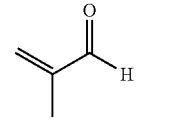

B-14

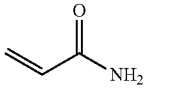

B-15

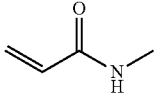

B-16

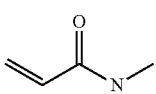

B-17

In the present invention, the reaction temperature is not particularly limited, but is preferably within a range of 0° C. to 100° C. or less. At temperatures of 100° C. or higher, a decrease in the reactivity is observed in some cases. This is considered to be because side reactions such as polymerization and decomposition of the α,β-unsaturated carbonyl compound (acrylic compound or the like) represented by the formula (B) results in proceeding, and the reactivity remarkably decreases.

The reaction time is not particularly limited, but the reaction is usually carried out in the range of 30 minutes to 24 hours.

As for the reaction conditions, the reaction can be carried out in the air or in an inert gas atmosphere (nitrogen or rare gas such as argon).

In order to stop the reaction, ice water may be added, or the reaction liquid may be neutralized with a base such as sodium hydroxide which has been cooled to about 4° C.

Various purification operations may be carried out as post-treatment of the reaction. Extraction, column purification, distillation, sublimation purification, recrystallization and the like can be appropriately used.

A chemical compound represented by formula (C), (F), (H), (J), (L), (N), (P) or (R) which is obtained by the production method of the present invention can be converted into a chemical compound having a substituent represented by the formula(S), by a reduction reaction. The reducing agent is not particularly limited, but examples thereof include the following agents: sodium borohydride, lithium borohydride, calcium borohydride, lithium aluminum hydride, lithium triethyl boron hydride, diisobutyl aluminum hydride, and sodium bis(2-methoxyethoxy)aluminum hydride.

The chemical compound having a substituent represented by the formula(S) is useful as a reaction intermediate for a charge transport material having a cross-linkable group. Specifically, the chemical compound can cause a chemical compound having a cross-linkable group to bond to the alcohol substituent and form an arylamine compound having a substituent represented by the formula (T), which has the cross-linkable group. The chemical compound having a substituent represented by the formula (T) can be dissolved in a solvent to form a coating film of a coating liquid, and form a charge transporting layer when the coating film is dried and/or cured. Examples of a polymerizable group include radical polymerizable functional groups such as a styryl group, a vinyl group, an acryloyloxy group, and a methacryloyloxy group.

Examples of a method of curing the coating film include a method of polymerizing the above chemical compound with heat, light (ultraviolet ray or the like), or radiation (electron beams or the like). Among the methods, the radiation is preferable, and among the radiations, the electron beams are more preferable.

EMBODIMENTS

The present invention will be described in more detail below with reference to specific Examples, but the present invention should not be construed as being limited thereto.

Example 1

A bisalkyl esterified compound 1 was synthesized by a reaction represented by the following reaction equation 1.

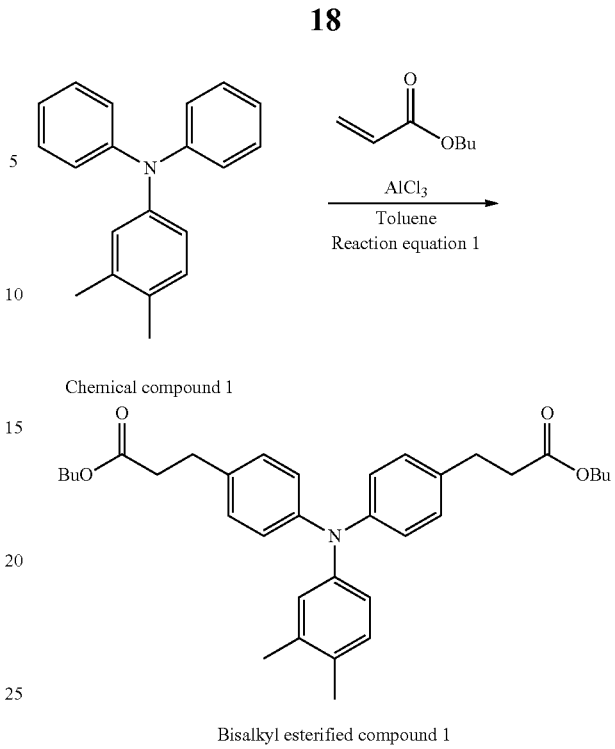

Chemical compound 1

Bisalkyl esterified compound 1

Under a nitrogen atmosphere, one grain of dibutylhydroxytoluene, 2.44 g (18.3 mmol) of aluminum chloride, and 7.30 mL of toluene were added to the flask, and the mixture was cooled to 4° C. or lower.

To the mixture, 2.62 mL (18.3 mmol) of butyl acrylate was added, and the resultant mixture was stirred for about 10 minutes.

To the mixture, 0.5 g (1.83 mmol) of N,N-diphenyl-3,4-xylidine (chemical compound 1) was added, and the reaction liquid was heated to 75° C. and stirred for 24 hours.

The obtained reaction liquid was cooled to 4° C. or lower, and was neutralized with an aqueous solution of sodium hydroxide.

To the liquid, 30 mL of ethyl acetate was added, and an organic substance was extracted. The collected organic layer was dried with sodium sulfate, and concentrated.

As a result of HPLC measurement of the obtained crude product, an elution time was 10.3 minutes (where methanol/water=90/10 was used as developing solvent, and absorption wavelength of 300 nm was used for detection); and the result of LC-MS was as follows; m/z: 530 (ionization method: APCI [M+1] 1H adduct).

A percentage value of an HPLC area of the bisalkyl esterified compound 1 was 68%.

The crude product was subjected to purification by silica gel column chromatography (toluene/methanol=97/3), and thereby 0.485 g (yield: 50%) of bisalkyl esterified compound 1 was obtained as a white-brown viscous body.

Examples 2 to 4

The operation was performed in the same manner as in Example 1, except that the usages of aluminum chloride and butyl acrylate were changed from Example 1.

The results of Examples 1 to 4 are shown in Table 1.

TABLE 1

| | Amount of butyl acrylate (mmol) | Amount of aluminum chloride (mmol) | Temperature (° C.) | Reaction time (hours) | Objective product HPLC area (%) | Yield (%) |
|---|---|---|---|---|---|---|
| Example 1 | 18.3 | 18.3 | 75 | 24.0 | 68 | 50 |
| Example 2 | 9.15 | 9.15 | 75 | 24.0 | 61 | 46 |
| Example 3 | 3.84 | 3.84 | 75 | 24.0 | 20 | — |
| Example 4 | 3.84 | 0.915 | 75 | 24.0 | 5 | — |

In Examples 3 and 4, it was confirmed that the reaction proceeded even after 24 hours though in a trace amount. From the results shown in Table 1, it is understood that the reactivity enhances when excessive amounts of Lewis acid (in this case, aluminum chloride) and acrylic acid ester exist.

Example 5

(Enhancement of Reactivity by Addition of Alcohol)
The bisalkyl esterified compound 1 was synthesized by a reaction represented by the following reaction equation 2.

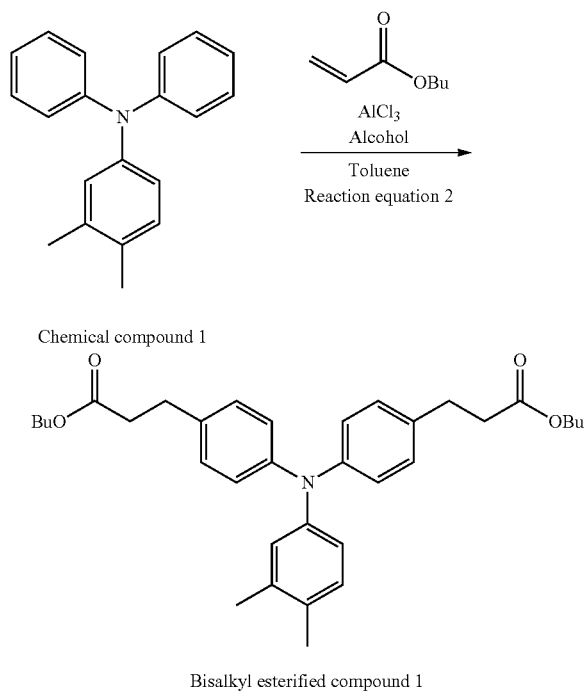

Under a nitrogen atmosphere, one grain of dibutylhydroxytoluene, 2.44 g (18.3 mmol) of aluminum chloride, and 7.30 mL of toluene were added to a flask, and the mixture was cooled to 4° C. or lower.

To the mixture, 1.67 mL (18.3 mmol) of 1-butanol was added, and the resultant mixture was stirred for about 10 minutes until the aluminum chloride dissolved.

To the mixture, 2.62 mL (18.3 mmol) of butyl acrylate was added, and the resultant mixture was stirred for about 5 minutes until the reaction liquid became light red.

Subsequently, 0.5 g (1.83 mmol) of N,N-diphenyl-3,4-xylidine (chemical compound 1) was added thereto, and the reaction liquid was heated to 75° C. and stirred for 6 hours.

The obtained reaction liquid was cooled to 4° C. or lower, and was neutralized with an aqueous solution of sodium hydroxide.

To the liquid, 30 mL of ethyl acetate was added, and an organic substance was extracted. The collected organic layer was dried with sodium sulfate, and concentrated.

The obtained crude product was subjected to the HPLC measurement in the same manner as in Example 1. The percentage value of the HPLC area of the bisalkyl esterified compound 1 was 69%.

The crude product was subjected to purification by silica gel column chromatography (toluene/methanol=97/3), and 0.475 g (yield: 49%) of bisalkyl esterified compound 1 was obtained as a white-brown viscous body.

Examples 6 to 10

The operation was performed in the same manner as in Example 5, except that the type and amount of the alcohol added, the temperature and the reaction time were changed from Example 5.

The results of Examples 5 to 10 are shown in Table 2.

TABLE 2

| | Alcohol | Alcohol (mmol) | Temperature (° C.) | Reaction time (hours) | Objective product HPLC area (%) | Yield (%) |
|---|---|---|---|---|---|---|
| Example 5 | 1-Butanol | 18.3 | 75 | 6.0 | 69 | 49 |
| Example 6 | 1-Butanol | 9.15 | 75 | 24.0 | 51 | 38 |
| Example 7 | 1-Butanol | 36.6 | 75 | 24.0 | 36 | 21 |
| Example 8 | 1-Butanol | 18.3 | 100 | 2.5 | 71 | 51 |
| Example 9 | Ethylene glycol | 9.15 | 100 | 2.5 | 64 | 46 |
| Example 10 | Cyclopentanol | 18.3 | 100 | 2.5 | 19 | — |

When the Example 5 shown in Table 2 is compared with the Example 1 shown in Table 1, it is understood that the reaction time was shortened from 24.0 hours to 6.0 hours by the addition of 1-butanol. It was confirmed that the yields were also equal. When a monohydric alcohol is used (in this case, 1-butanol), it is understood that it is preferable to add the monohydric alcohol in the same equivalent as that of Lewis acid (in this case, aluminum chloride). In addition, it is understood that a dihydric alcohol (ethylene glycol in this case) shows equal reactivity.

In Example 10, the production of the objective product decreased, and accordingly, a decrease in the reactivity was observed as the number of carbon atoms of the alcohol increased.

Example 11

(Influence of Type of Lewis Acid or Sulfonic Acid)

The bisalkyl esterified compound 1 was synthesized by a reaction represented by the following reaction equation 3.

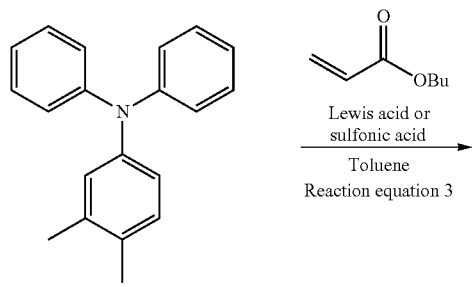

Chemical compound 1

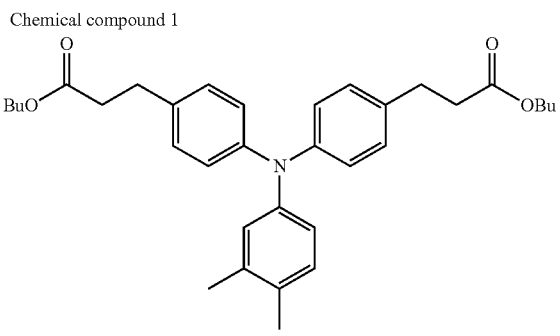

Bisalkyl esterified compound 1

Under a nitrogen atmosphere, one grain of dibutylhydroxytoluene, 5.02 mL (18.3 mmol) of boron trifluoride diethyl ether complex, and 7.30 mL of toluene were added to a flask, and the mixture was cooled to 4° C. or lower.

To the mixture, 2.62 mL (18.3 mmol) of butyl acrylate was added, and the resultant mixture was stirred for about 10 minutes.

To the mixture, 0.5 g (1.83 mmol) of N,N-diphenyl-3,4-xylidine (chemical compound 1) was added, and the reaction liquid was heated to 100° C. and stirred for 7 hours.

The obtained reaction liquid was cooled to 4° C. or lower, and was neutralized with an aqueous solution of sodium hydroxide.

To the liquid, 30 mL of ethyl acetate was added, and an organic substance was extracted. The collected organic layer was dried with sodium sulfate, and concentrated. The percentage value of the HPLC area of the bisalkyl esterified compound 1 was 24%.

The concentrate was subjected to purification by silica gel column chromatography (toluene/methanol=97/3), and 0.233 g (yield: 24%) of bisalkyl esterified compound 1 was obtained as a white-brown viscous body.

Examples 12 to 18

The operation was performed in the same manner as in Example 11, except that the type of Lewis acid was changed as shown in Table 3, from Example 11.

Comparative Examples 1 and 2

The operation was performed in the same manner as in Example 11, except that the Lewis acid was changed as shown in Table 3, from Example 11.

The results of Examples 11 to 18 and Comparative Examples 1 and 2 are shown in Table 3.

TABLE 3

| | Lewis acid | Reaction temperature (° C.) | Reaction time (hours) | Objective product HPLC area (%) | Yield |
|---|---|---|---|---|---|
| Example 11 | Boron trifluoride diethyl ether | 100 | 7.0 | 24% | 24% |
| Example 12 | Titanium tetrachloride | 100 | 1.0 | Trace amount | — |
| Example 13 | Iron chloride (III) | 100 | 1.0 | Trace amount | — |
| Example 14 | Aluminum bromide | 100 | 7.0 | 65% | 46% |
| Example 15 | Zinc chloride | 100 | 7.0 | Trace amount | — |
| Example 16 | Methanesulfonic acid | 100 | 5.0 | 49% | 38% |
| Example 17 | Trifluoromethanesulfonic acid | 50 | 5.0 | 63% | 51% |
| Example 18 | (+)-10-camphorsulfonic acid | 100 | 7.0 | Trace amount | — |
| Comparative Example 1 | Hydrochloric acid | 100 | 7.0 | — | — |
| Comparative Example 2 | Trifluoroacetic acid | 100 | 7.0 | — | — |

In Examples 14, 16 and 17, it was confirmed that the objective product was produced in a relatively high yield. In addition, in Examples 12, 13, 15 and 18, the production of the objective product was confirmed though in a trace amount. In Comparative Examples 1 and 2, the reaction was carried out for 7 hours, but almost 100% of the raw materials were recovered, and it was confirmed that the reaction did not proceed. It is understood that in the production method of the present invention, the reaction proceeds in the presence of Lewis acid and sulfonic acid.

Example 19

(Change in Type of α,β-Unsaturated Carbonyl Compound (Formula (B)))

The bisalkyl esterified compound 2 was synthesized by a reaction represented by the following reaction equation 4.

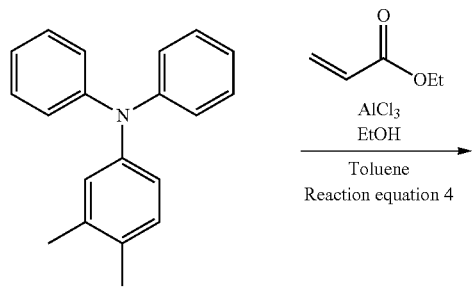

Chemical compound 1

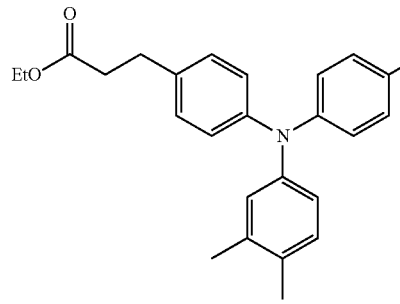

Bisalkyl esterified compound 2

Under a nitrogen atmosphere, one grain of dibutylhydroxytoluene, 2.44 g (18.3 mmol) of aluminum chloride, and 7.30 mL of toluene were added to a flask, and the mixture was cooled to 4° C. or lower.

To the mixture, 1.07 mL (18.3 mmol) of ethanol was added, and the resultant mixture was stirred for about 10 minutes.

To the mixture, 1.99 mL (18.3 mmol) of ethyl acrylate was added, and the resultant mixture was stirred for about 5 minutes.

Subsequently, 0.5 g (1.83 mmol) of N,N-diphenyl-3,4-xylidine (chemical compound 1) was added thereto, and the reaction liquid was heated to 75° C. and stirred for 6 hours.

The obtained reaction liquid was cooled to 4° C. or lower, and was neutralized with an aqueous solution of sodium hydroxide.

To the liquid, 30 mL of ethyl acetate was added, and an organic substance was extracted. The collected organic layer was dried with sodium sulfate, and concentrated.

As a result of the HPLC measurement of the obtained chemical compound, an elution time was 6.9 minutes (where methanol/water=90/10 was used as developing solvent, and absorption wavelength of 300 nm was used for detection); and the result of LC-MS was as follows; m/z: 474 (ionization method: APCI [M+1] 1H adduct).

The concentrate was subjected to purification by silica gel column chromatography (toluene/methanol=97/3), and thereby 0.451 g (yield: 52%) of bisalkyl esterified compound 2 was obtained as a white-brown viscous body.

Example 20

Enhancement of Reactivity by Combination of Plurality of Lewis Acids and Sulfonic Acids The bisalkyl esterified compound 1 was synthesized by a reaction represented by the following reaction equation 5.

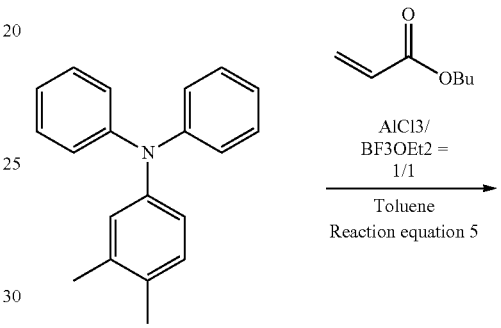

Chemical compound 1

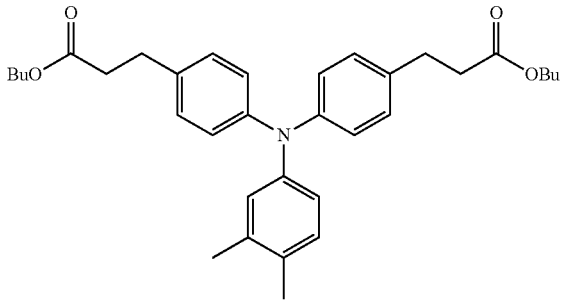

Bisalkyl esterified compound 1

Under a nitrogen atmosphere, one grain of dibutylhydroxytoluene, and 7.30 mL of toluene were added to a flask, and the mixture was cooled to 4° C. or lower.

To the mixture, 0.537 g (4.03 mmol) of aluminum chloride, 1.1 mL (4.03 mmol) of boron trifluoride diethyl ether complex, and 0.573 mL (4.03 mmol) of butyl acrylate were added, and the resultant mixture was stirred for about 10 minutes.

To the mixture, 0.5 g (1.83 mmol) of N,N-diphenyl-3,4-xylidine (chemical compound 1) was added, and the reaction liquid was stirred at room temperature for 7 hours.

The obtained reaction liquid was cooled to 4° C. or lower, and was neutralized with an aqueous solution of sodium hydroxide.

To the liquid, 30 mL of ethyl acetate was added, and an organic substance was extracted. The collected organic layer was dried with sodium sulfate, and concentrated. A percentage value of the HPLC area of the bisalkyl esterified compound 1 was 68%.

The concentrate was subjected to purification by silica gel column chromatography (toluene/methanol=97/3), and thereby 0.581 g (yield: 60%) of bisalkyl esterified compound 1 was obtained as a white-brown viscous body.

Example 21

The operation was performed in the same manner as in Example 20, except that the reaction conditions were set in the following way.

To the conditions of Example 20, 24 μL (0.37 mmol, 20 mol % of amine compound) of methanesulfonic acid was further added. The results are shown in Table 4.

Example 22

The operation was performed in the same manner as in Example 20, except that the reaction conditions were set in the following way.

To the conditions of Example 20, 127 mg (0.55 mmol, 30 mol % of amine compound) of (+)-10-camphorsulfonic acid was further added. The results are shown in Table 4.

TABLE 4

|  | Types of sulfonic acid | Amount of charged sulfonic acid (mmol) | Reaction temperature | Reaction time (hours) | Objective product HPLC area (%) | Yield |
|---|---|---|---|---|---|---|
| Example 20 | — | — | Room temperature | 7.0 | 68% | 60% |
| Example 21 | Methanesulfonic acid | 20 | Room temperature | 7.0 | 70% | 62% |
| Example 22 | (+)-10-camphorsulfonic acid | 30 | Room temperature | 7.0 | 83% | 65% |

In Example 20, the reactivity was greatly enhanced by simultaneous use of the boron trifluoride diethyl ether complex and aluminum chloride. It is assumed that by the simultaneous use of the above two Lewis acids, boron trichloride was produced in the reaction system, which suppressed the reduction in the electron density of arylamine. In Examples 21 and 22, the respective sulfonic acids were further used simultaneously with the above two Lewis acids, thereby the reactivity was further enhanced, and the purity and yield of the objective product were enhanced.
(Change of Arylamine of Raw Material)

Example 23

A monoalkyl esterified compound 3 was synthesized by a reaction represented by the following reaction equation 6.

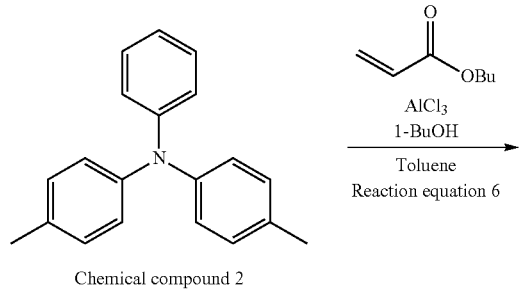

Chemical compound 2

-continued

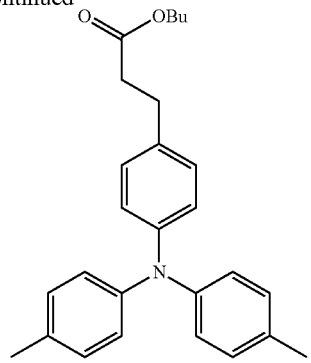

Monoalkyl esterified compound 3

Under a nitrogen atmosphere, one grain of dibutylhydroxytoluene, and 44.0 mL of toluene were added to a flask, and the mixture was cooled to 4° C. or lower.

To the mixture, 7.32 g (54.9 mmol) of aluminum chloride and 5.02 mL (54.9 mmol) of 1-butanol were added, and the resultant mixture was stirred for about 10 minutes.

To the mixture, 7.87 mL (54.9 mmol) of butyl acrylate was added, and the resultant mixture was stirred for about 5 minutes.

Subsequently, 3.0 g (11.0 mmol) of 4-methyl-N-phenyl-N-(p-tolyl) aniline (chemical compound 2) was added thereto, and the reaction liquid was heated to 75° C. and stirred for 7 hours.

The obtained reaction liquid was cooled to 4° C. or lower, and was neutralized with an aqueous solution of sodium hydroxide.

To the liquid, 120 mL of ethyl acetate was added, and an organic substance was extracted. The collected organic layer was dried with sodium sulfate, and concentrated. As a result of the HPLC measurement of the obtained chemical compound, an elution time was 8.1 minutes (where methanol/water=90/10 was used as developing solvent, and absorption wavelength of 300 nm was used for detection); and the result of LC-MS was as follows; m/z: 401 (ionization method: APCI [M+1] 1H adduct).

The concentrate was subjected to purification by silica gel column chromatography (toluene), and 4.14 g (yield: 94%) of monoalkyl esterified compound 3 was obtained as a white-brown viscous body.

Examples 24 to 27

Reactions were carried out in the same method as in Example 16 with the following respective compounds 3 to 6. The production of the objective product was confirmed by HPLC and LC-MS. The reaction was carried out with 0.5 g of arylamine of the raw material, and the usages of butyl acrylate, aluminum chloride and 1-butanol were 5 to 20 equivalents relative to the arylamine; and the reaction was carried out at a temperature of 100° C.
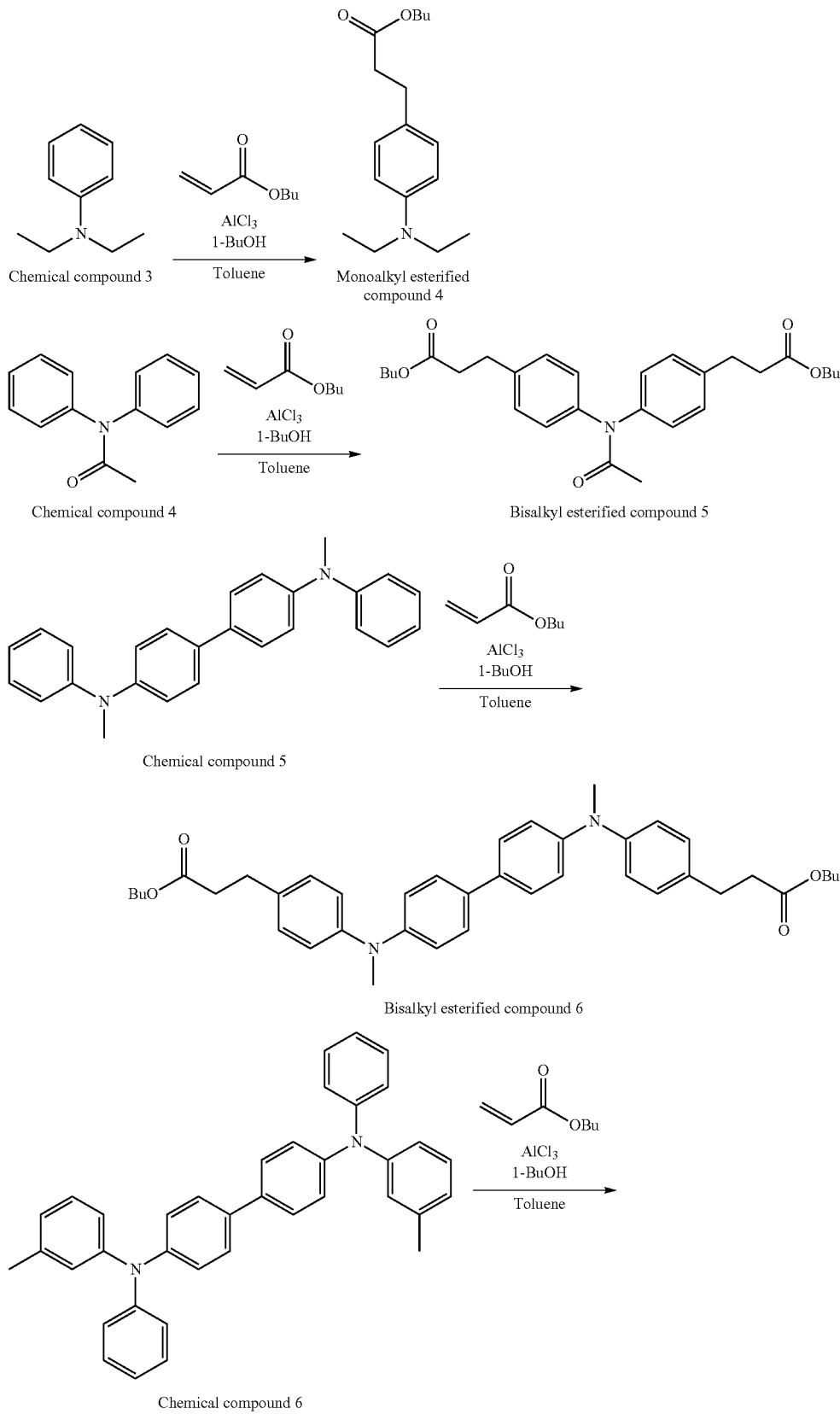

-continued

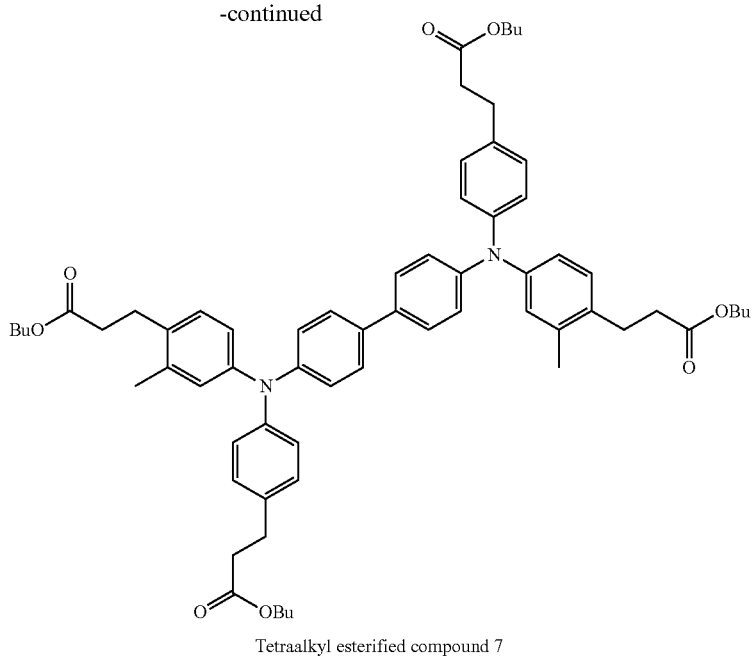

Tetraalkyl esterified compound 7

The results of Examples 24 to 27 are shown in Table 5.

TABLE 5

|  | Arylamine | Amount of butyl acrylate (mmol) | Amount of aluminum chloride (mmol) | Amount of 1-butanol (equivalent) | Reaction temperature (° C.) | Reaction time (hours) | HPLC area (%) |
| --- | --- | --- | --- | --- | --- | --- | --- |
| Example 24 | Chemical compound 3 | 5 | 5 | 5 | 100 | 3.0 | 86 |
| Example 25 | Chemical compound 4 | 10 | 10 | 10 | 100 | 3.0 | 76 |
| Example 26 | Chemical compound 5 | 10 | 10 | 10 | 100 | 3.0 | 59 |
| Example 27 | Chemical compound 6 | 20 | 20 | 20 | 100 | 3.0 | 43 |

Example 28

(Reduction Reaction)

A bisalcoholized compound 8 was synthesized by a reaction represented by the following reaction equation 7.

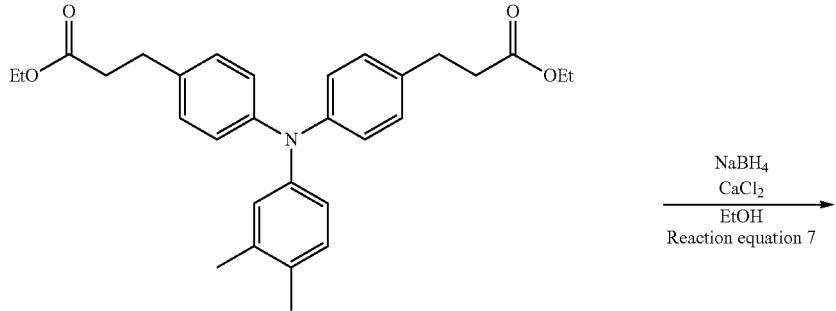

Bisalkyl esterified compound 2

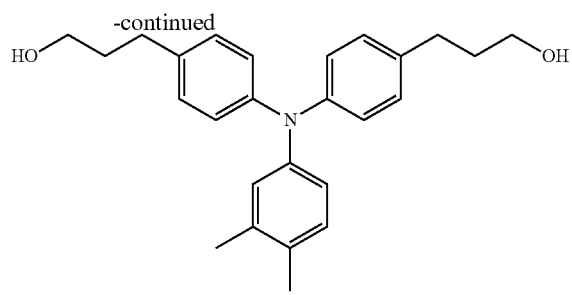

Bisalcoholized compound 8

Under an air atmosphere, 9.0 g of bisalkyl esterified compound 2, 100 mL of ethanol, and 8.42 g of calcium chloride were added to a flask, and the reaction liquid was refluxed.

To the mixture, 5.47 g of sodium borohydride was added in several batches over 30 minutes. After that, the reaction liquid was stirred under a reflux condition for 3 hours. The obtained reaction liquid was cooled to 4° C. or lower, and was neutralized with an aqueous solution of hydrogen chloride. To the liquid, 400 mL of ethyl acetate was added, and an organic substance was extracted. The collected organic layer was dried with sodium sulfate, and concentrated.

The above concentrate was subjected to purification by silica gel column chromatography (ethyl acetate/heptane=1/2), and 6.06 g (yield: 82%) of bisalcoholized compound 8 was obtained as a white solid.

Example 29

(Acrylating Reaction)

A bisacrylated compound 9 was synthesized by a reaction represented by the following reaction equation 8.

Under an atmospheric atmosphere, 4.57 g of bisalcoholized compound 8, 18 mL of toluene, 15 mg of 4-methoxyphenol (MEHQ), 2 mL of acrylic acid, and 225 mg of p-toluenesulfonic acid monohydrate (PTSA) were added to a flask. This reaction liquid was stirred under a reflux condition for 3 hours.

The obtained reaction liquid was cooled to room temperature, and water was added thereto. To the liquid, 50 mL of toluene was added, and an organic substance was extracted. As for the extraction, an aqueous layer was washed with toluene three times, and an organic layer was washed with water twice.

The collected organic layer was dried with sodium sulfate, and concentrated. The above concentrate was subjected to purification by silica gel column chromatography (toluene), and 3.46 g (yield: 59%) of bisacrylated compound 9 was obtained as a white-brown viscous body.

Example 30

(Production of Electrophotographic Photosensitive Member)

The parts shown in the present Example are parts by mass.

A coating liquid for a protective layer (coating liquid for surface layer) was prepared by dissolving 4 parts of the

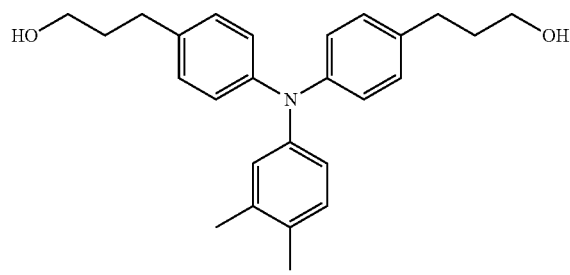

Bisalcoholized compound 8

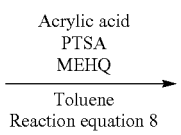

Acrylic acid
PTSA
MEHQ
———————→
Toluene
Reaction equation 8

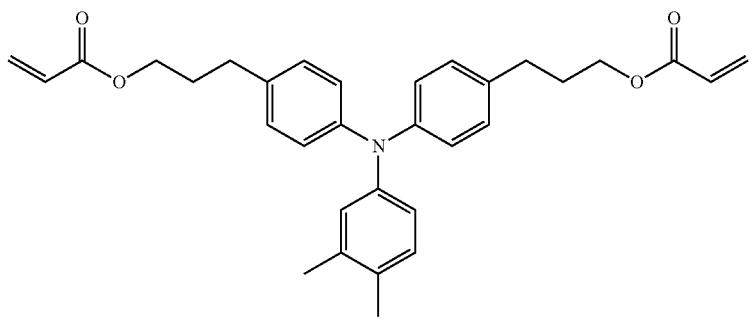

Bisacrylated compound 9 chemical compound represented by the bisacrylated compound 9 obtained in Example 29 in 100 parts of tetrahydrofuran. The coating liquid for the protective layer was spray-coated on the positive-hole transport layer to form a coating film; and the obtained coating film was dried at 50° C. for 10 minutes, and was subjected to polymerization curing treatment by electron beam irradiation and heating. Next, the above sample was taken out to the atmosphere, and was further heated at 100° C. for 10 minutes; and thereby the protective layer (surface layer) was formed of which the film thickness was 5 μm.

According to one aspect of the present disclosure, an alkyl-esterified arylamine compound can be produced by conjugate adding α,β-unsaturated carbonyl substituent to an arylamine compound that constitutes a charge transport material, in a small number of steps. The production method of the present disclosure has such an advantage that halogenation is not required and the product after the addition reaction is already saturated alkyl chain. Because of this, a method of four stages (halogenation, Heck reaction, reduction of unsaturated bond, and reduction of ester) can be greatly simplified which have been used until now when the alcohol form of the arylamine compound has been synthesized, and the alcohol form of the arylamine compound can be easily produced in as small number of steps as two stages (the present disclosure and reduction of ester). In addition, an electrophotographic photosensitive member can be produced that uses the alkyl-esterified arylamine compound.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2021-177592, filed Oct. 29, 2021, which is hereby incorporated by reference herein in its entirety.

What is claimed is:

1. A method for producing an arylamine compound represented by formula (C), the method comprising an addition reaction, as a Friedel-Crafts reaction, of adding a chemical compound represented by formula (B) to a carbon atom bonded to a hydrogen atom on a benzene ring of a chemical compound represented by formula (A), in the presence of one or more acids selected from the group consisting of Lewis acids and sulfonic acids, to produce the arylamine compound:

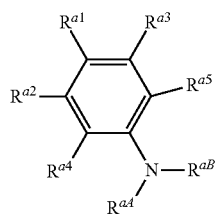

(A)

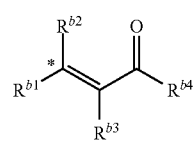

(B)

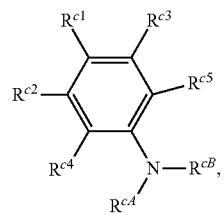

(C)

wherein:

in the formula (A), $R^{a1}$, $R^{a2}$, $R^{a3}$, $R^{a4}$, and $R^{a5}$ each independently represent a hydrogen atom or an alkyl group, at least one of $R^{a1}$, $R^{a2}$, $R^{a3}$, $R^{a4}$, and $R^{a5}$ is the hydrogen atom, and $R^{aA}$ and $R^{aB}$ each independently represent an unsubstituted or substituted alkyl group, an unsubstituted or substituted aryl group, an acyl group, or an oxycarbonyl group;

in the formula (B), $R^{b1}$, $R^{b2}$ and $R^{b3}$ each independently represent a hydrogen atom or a methyl group, $R^{b4}$ represents a hydrogen atom, a hydroxy group, an unsubstituted or substituted alkoxy group, an unsubstituted or substituted amino group, an unsubstituted or substituted alkyl group, an unsubstituted or substituted aryl group, or an unsubstituted or substituted aryloxy group, and * represents a carbon atom position bonding with the formula (A); and in the formula (C), $R^{c1}$, $R^{c2}$, $R^{c3}$, $R^{c4}$, and $R^{c5}$ each independently represent a hydrogen atom, an alkyl group, or a monovalent group represented by formula (D), such that at least one of $R^{c1}$, $R^{c2}$, $R^{c3}$, $R^{c4}$, and $R^{c5}$ is the monovalent group represented by the formula (D), and $R^{cA}$ and $R^{cB}$ each independently represent an unsubstituted or substituted alkyl group, an unsubstituted or substituted aryl group, an acyl group, or an oxycarbonyl group; and:

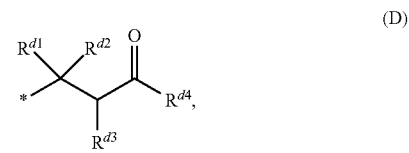

(D)

wherein, in the formula (D), $R^{d1}$, $R^{d2}$, and $R^{d3}$ each independently represent a hydrogen atom or a methyl group, $R^{d4}$ represents a hydrogen atom, a hydroxy group, an unsubstituted or substituted alkoxy group, an unsubstituted or substituted amino group, an unsubstituted or substituted alkyl group, an unsubstituted or substituted aryl group, or an unsubstituted or substituted aryloxy group, and * represents a bonding position.

2. The method for producing the arylamine compound according to claim 1, wherein:

the chemical compound represented by the formula (A) is a chemical compound represented by formula (E); and the chemical compound represented by the formula (C) is a chemical compound represented by formula (F):

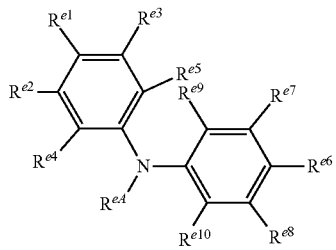

(E)

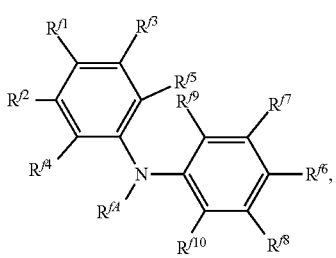

(F)

wherein:
in the formula (E), $R^{e1}$, $R^{e2}$, $R^{e3}$, $R^{e4}$, $R^{e5}$, $R^{e6}$, $R^{e7}$, $R^{e8}$, $R^{e9}$, and $R^{e10}$ each independently represent a hydrogen atom or an alkyl group, at least one of $R^{e1}$, $R^{e2}$, $R^{e3}$, $R^{e4}$, $R^{e5}$, $R^{e6}$, $R^{e7}$, $R^{e8}$, $R^{e9}$, and $R^{e10}$ represents the hydrogen atom, $R^{eA}$ represents an unsubstituted or substituted alkyl group, an unsubstituted or substituted aryl group, an acyl group, or an oxycarbonyl group; and in the formula (F), $R^{f1}$, $R^{f2}$, $R^{f3}$, $R^{f4}$, $R^{f5}$, $R^{f6}$, $R^{f7}$, $R^{f8}$, $R^{f9}$, and $R^{f10}$ each independently represent a hydrogen atom, an alkyl group, or a monovalent group represented by the formula (D), and $R^{fA}$ represents an unsubstituted or substituted alkyl group, an unsubstituted or substituted aryl group, an acyl group, or an oxycarbonyl group.

3. The method for producing the arylamine compound according to claim 2, wherein:
the chemical compound represented by the formula (E) is a chemical compound represented by formula (G); and
the chemical compound represented by the formula (F) is a chemical compound represented by formula (H):

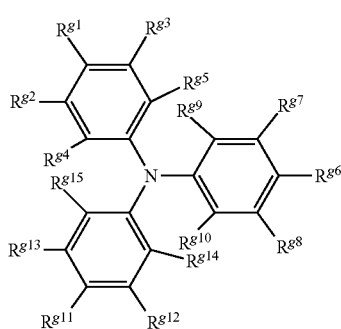

(G)

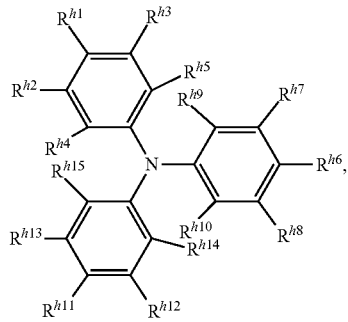

(H)

wherein:
in the formula (G), $R^{g1}$, $R^{g2}$, $R^{g3}$, $R^{g4}$, $R^{g5}$, $R^{g6}$, $R^{g7}$, $R^{g8}$, $R^{g9}$, $R^{g10}$, $R^{g11}$, $R^{g12}$, $R^{g13}$, $R^{g14}$, and $R^{g15}$ each independently represent a hydrogen atom or an alkyl group, and at least one of $R^{g1}$, $R^{g2}$, $R^{g3}$, $R^{g4}$, $R^{g5}$, $R^{g6}$, $R^{g7}$, $R^{g8}$, $R^{g9}$, $R^{g10}$, $R^{g11}$, $R^{g12}$, $R^{g13}$, $R^{g14}$, and $R^{g15}$ represents the hydrogen atom; and in the formula (H), $R^{h1}$, $R^{h2}$, $R^{h3}$, $R^{h4}$, $R^{h5}$, Rho, $R^{h7}$, $R^{h8}$, $R^{h9}$, $R^{h10}$, $R^{h11}$, $R^{h12}$, $R^{h13}$, $R^{h14}$, and $R^{h15}$ each independently represent a hydrogen atom, an alkyl group, or a monovalent group represented by the formula (D).

4. The method for producing the arylamine compound according to claim 1, wherein the same equivalent of alcohol as that of the Lewis acid is added.

5. The method for producing the arylamine compound according to claim 4, wherein as the alcohol, a monohydric alcohol having 4 or less carbon atoms or a dihydric alcohol having 4 or less carbon atoms is added.

6. The method for producing the arylamine compound according to claim 1, wherein as the Lewis acids, one or more Lewis acids are used that are selected from the group consisting of aluminum chloride, aluminum bromide and boron trifluoride.

7. The method for producing the arylamine compound according to claim 1, wherein as the Lewis acids, two or more different Lewis acids are simultaneously used.

8. The method for producing the arylamine compound according to claim 7, wherein as the Lewis acids, aluminum chloride and boron trifluoride are simultaneously used.

9. The method for producing the arylamine compound according to claim 1, wherein as the sulfonic acids, one or more sulfonic acids are used that are selected from the group consisting of methanesulfonic acid, trifluoromethanesulfonic acid, and camphorsulfonic acid.

10. The method for producing the arylamine compound according to claim 1, wherein the Lewis acids and the sulfonic acids are simultaneously used.

11. The method for producing the arylamine compound according to claim 10, wherein as the Lewis acids, aluminum chloride and boron trifluoride are simultaneously used, and as the sulfonic acids, one or more sulfonic acids are simultaneously used that are selected from the group consisting of methanesulfonic acid and camphorsulfonic acid.

12. The method for producing the arylamine compound according to claim 1, wherein:
the chemical compound represented by the formula (A) is a chemical compound represented by formula (U);
the chemical compound represented by the formula (B) is a chemical compound represented by formula (V);
the chemical compound represented by the formula (C) is a chemical compound represented by formula (W); and the monovalent group represented by the formula (D) is a monovalent group represented by formula (X):

(u) [structure: triphenylamine with methyl substituent — N,N-diphenyl-3,4-dimethylaniline-like]

(v) [structure: butyl acrylate, CH2=CH-C(=O)-OBu]

(w) [structure: bis(4-(3-butoxy-3-oxopropyl)phenyl)-(3,4-dimethylphenyl)amine]

(x) [structure: *-CH2-CH2-C(=O)-OBu]

13. The method for producing the arylamine compound according to claim 1, wherein $R^{a1}$ in the formula (A) is a hydrogen atom, and the chemical compound represented by the formula (B) is added selectively to the carbon atom bonded to the hydrogen atom to introduce the monovalent group represented by the formula (D) and thereby produce the chemical compound represented by the formula (C).

14. The method for producing the arylamine compound according to claim 2, wherein at least one of $R^{e1}$ and $R^{e6}$ in the formula (E) is a hydrogen atom, and the chemical compound represented by the formula (B) is added selectively to the carbon atom bonded to the hydrogen atom to introduce the monovalent group represented by the formula (D) and thereby produce the chemical compound represented by the formula (F).

15. The method for producing the arylamine compound according to claim 3, wherein at least one of the $R^{g1}$, the $R^{g6}$, and the $R^{g11}$ in the formula (G) is a hydrogen atom, and the chemical compound represented by the formula (B) is added selectively to the carbon atom bonded to the hydrogen atom to introduce the monovalent group represented by the formula (D) and thereby produce the chemical compound represented by the formula (H).

* * * * *